United States Patent [19]

Hoy et al.

[11] Patent Number: 5,702,932
[45] Date of Patent: Dec. 30, 1997

[54] MICROINJECTION METHODS TO TRANSFORM ARTHROPODS WITH EXOGENOUS DNA

[75] Inventors: Marjorie A. Hoy; James K. Presnail, both of Gainsville, Fla.

[73] Assignees: University of Florida, Gainesville, Fla.; University of California, Oakland, Calif.

[21] Appl. No.: 479,485

[22] Filed: Jun. 7, 1995

Related U.S. Application Data

[63] Continuation of Ser. No. 95,455, Jul. 20, 1993, abandoned, which is a continuation-in-part of Ser. No. 917,703, Jul. 20, 1992, abandoned.

[51] Int. Cl.$^6$ .............................. C12N 15/00; C12N 5/00
[52] U.S. Cl. .................... 435/172.3; 800/2; 800/DIG. 1; 935/53; 935/63
[58] Field of Search ........................... 800/2, DIG. 1; 435/172.3; 424/9.1; 934/53, 63

[56] References Cited

U.S. PATENT DOCUMENTS 5,159,135  10/1992  Umbeck .

OTHER PUBLICATIONS

Presnail et al (1995) J. Cell Biol. 21A, 266.
Saunders et al (1989) Nucl. Acids Res. 17, 6205–6215.
Sabelis, M.W. (1985) "Life History–Capacity for Population Increase" In: Spider Mites: Their Biology, Natural Enemies, and Control 1B:35–40.
Chant, D.A. (1985) "External Anatomy" In: Spider Mites: Their Biology, Natural Enemies, and Control 1B:5–33.
Headley, J.C., M.A. Hoy (1986) "The Economics of Integrated Mice Management in Almonds"California Agriculture Jan–Feb:38–30.
Hoy, Marjorie A. (1990) "Pesticide Resistance in Arthropod Natural Enemies: Variability and Selection Responses" In: Pesticide Resistance in Arthropods 203–236.
Beckendorf, S.K., M.A. Hoy (1985) "Genetic Improvement of Arthropod Natural Enemies Through Selection, Hybridization or Genetic Engineering Techniques" In: Biological Control in Agricultural IPM Systems 167–187.
Vasil, Vimla et al. (1992) "Herbicide Resistant Fertile Transgenic Wheat Plants Obtained by Microprojectile Bombardment of Regenerable Embryogenic Callus" Bio/Technology 10:667–674.

Fire, Andrew (1986) "Integrative Transformation of *Caenorhabditis elegans*" The EMBO Journal 5(10):2673–2680.
Spradling, A.C., G.M. Rubin (1982) "Transposition of Cloned Elements into Drosophila Germ Line Chromosomes" Science 218:341–347.
Rubin, G.M., A.C. Spradling (1982) "Genetic Transformation of Drosophila with Transposable Element Vectors" Science 218:348–353.
Steller, H., V. Pirrotta (1985) "A Transposable P Vector that confers Selectable G418 Resistance to Drosophila Larvae" EMBO Journal 4(1):167–171.
Miller, Louis H. et al. (1987) "Stable Integration and Expression of a Bacterial Gene in the Mosquito *Anopheles gambia*" Science 237:779–781.
McGrane, Vicki et al. (1988) "Microinjection of DNA into *Aedes triseriatus* Ova and Detection of Integration" Am. J. Trop. Med. Hyg. 39:502–510.
Morris, Alison C. et al. (1989) "Genetic Transformation of the Mosquito *Aedes aegypti* by Microinjection of DNA" Med. Vet. Entomol. 3:1–7.
O'Brochta, D.A., A.M. Handler (1988) "Mobility of P Elements in Drosophilids and nondrosophilids" Proc. Natl. Acad. Sci. USA 84:6052–6056.
Baldarelli, R.M., J.A. Lengyel (1990) "Transient Expression of DNA after Ballistic Introduction into Drosophila embryos" Nucl. Acids Res. 18:5903–5904.
Carlson, D.A.et al. (1989) "Advances in Insertion of Material into Insect Eggs via a Particle Shotgun Technique" Host Reg. Developmental Mechanisms in Vector Arthropods 248–252.
Milne, Charles P. Jr. et al. (1988) "Microinjection of Early Honeybee Embryos" Journal of Agricultural Research 27(2):84–89.
Presnail, J.K., M.A. Hoy (1992) "Stable Genetic Transformation of a Beneficial Anthropod, *Metaseiulus occidentalis* (Acari: Phytoseiidae), by a Microinjection Technique" Proc. Natl. Acad. Sci. USA 89:7732–7736.

*Primary Examiner*—Deborah Crouch
*Attorney, Agent, or Firm*—Saliwanchik, Lloyd & Saliwanchik

[57] ABSTRACT

This invention relates to methods for transforming arthropods with exogenous DNA. The methods are useful for arthropods that have not previously been amenable to DNA-mediated transformation, and also provide a simpler and more efficient means of transforming arthropods than have previously been described. The method involves microinjecting a nucleic acid sequence encoding a desired trait into the reproductive tract of a female arthropod before oviposition.

7 Claims, 3 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:1:

GCTCTTCTCC ACTCTGTCAC ACAGTAAACG GC        3 2

( 2 ) INFORMATION FOR SEQ ID NO:2:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:2:

CGCAAAGTAG ACACCACGTT GCCCGCGACC        3 0

( 2 ) INFORMATION FOR SEQ ID NO:3:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear     ( i i ) MOLECULE TYPE: DNA (synthetic)

( x i ) SEQUENCE DESCRIPTION: SEQ ID NO:3:

GGGCGCAATC GTAACCGTGC AATCTGCCAG        3 0

MICROINJECTION METHODS TO TRANSFORM ARTHROPODS WITH EXOGENOUS DNA

CROSS-REFERENCE TO A RELATED APPLICATION

This application is a continuation of application Ser. No. 08/095,455, filed Jul. 20, 1993, now abandoned, which is a continuation-in-part of application Ser. No. 07/917,703, filed Jul. 20, 1992, now abandoned.

BACKGROUND OF THE INVENTION

This invention relates to methods for transforming arthropods with exogenous DNA. The methods are useful for arthropods that have not previously been amenable to DNA-mediated transformation, and also provide a simpler and more efficient means of transforming arthropods that have previously been transformed.

Many arthropod species are disease vectors and a far greater number are agriculturally important, including those organisms that are pests, and those that are beneficial. Genetic manipulation of arthropods has the potential to be an extremely important means of altering properties of arthropods to, for example, reduce their ability to spread disease or to increase their effectiveness as biological control agents. It will be possible to modify the temperature tolerance, host range, resistance to insecticides, or sex ratio. Altering these traits could improve the performance of a biological control agent and result in an overall reduction in the use of insecticides.

Classical genetic manipulation of the western predatory mite *Metaseiulus occidentalis* (Nesbitt), for example, has proven to be highly valuable in using this mite as a biological control agent against spider mites. *M. occidentalis* is a member of the cosmopolitan family Phytoseiidae, a group of mostly predatory mites responsible for controlling spider mites and other arthropods in many crops (Sabelis, M. W. [1985] In: *Spider Mites: Their Biology, Natural Enemies, and Control*, eds. Helle, W. and Sabelis, M. W., Elsevier, N.Y., Vol. 1B, pp. 35–40). *M. occidentalis* is less than 500 µm long (Chant, D. A. [1985], Id. at pp. 3–32), and has five developmental stages: egg, larva, protonymph, deutonymph and adult. At 27° C. the life cycle from egg to gravid female is completed in approximately 6 days. Females lay approximately 2 eggs a day. Only one egg is matured at a time, with the fully mature egg occupying approximately ⅓ of the body cavity. Phytoseiids are thought to have a single unpaired ovary.

Using classical genetic methods, a process that required three years to accomplish, pesticide-resistant *M. occidentalis* strains were developed previously. These mites were incorporated into an integrated mite management program in California almond orchards and have saved almond growers at least $24–44 per acre each year, primarily by reducing pesticide applications to control spider mites (Headley, J. C., M. A. Hoy [1986] *California Agriculture*, Jan–Feb:28–30.

Genetic improvement of a beneficial arthropod species has thus been shown to be highly effective. Harmful arthropods may also be controlled by genetic manipulation. However, classical genetic techniques have significant drawbacks. Artificial selection may be slow, inefficient, or ineffective. Most genetic improvement projects involve selecting for resistance to pesticides (Hoy, M. A. [1990] In: *Pesticide Resistance in Arthropods*, eds. Roush, R. T. and B. E. Tabashnik; Chapman and Hall, N.Y., pp. 203–236), but sometimes resistance alleles do not occur in the populations that are being screened. Selection attempts may take more than 2 years, and success is not assured. The use of mutagenesis and hybridization for genetic manipulation remain extremely limited and have significant disadvantages (Beckendorf, S. K., M. A. Hoy [1985] In: *Biological Control in Agricultural IPM Systems*, Eds. Hoy, M. A. & D. C. Herzog, Academic Press, Orlando, pp. 167–187; Hoy, M. A. [1990], supra.). A more efficient method for developing genetically-improved strains of arthropod biological control agents is needed.

In recent years, substantial research efforts have been directed to the development of direct genetic manipulation techniques which can be utilized to develop plants and animals with useful traits. These techniques can yield highly desirable plants and animals much more quickly and efficiently than through the use of traditional breeding or selection techniques. Bacteria were the focus of much of the early genetic transformation work but, within the last decade, transformation of a wide variety of plants and animals has been attempted. Some of these transformation efforts have been successful (see, for example, Vasil, V., A. M. Castillo, M. E. Fromm, I. K. Vasil [1992] *Bio/Technology* 10:667–674; Umbeck, P. F., U.S. Pat. No. 5,159,135; Fire, A. [1986] *EMBO J.* 5(10):2673–2680; Spradling, A., G. Rubin [1982] *Science* 218:341–347; Rubin, G., A. Spradling [1982] *Science* 218:348–353), while many of the experiments have been unsuccessful. There remains a great number of organisms for which no method of transformation currently exists.

The development of germ-line transformation in *Drosophila melanogaster* (Spradling et al., supra) has provided a valuable tool for genetic analysis of this arthropod. Initial efforts to transform arthropods other than Drosophila focused on employing existing P element vectors, in particular pUChsneo (Steller, H., V. Pirrotta [1985] *EMBO J.* 4:167–171), and microinjecting this vector into preblastoderm eggs (Miller, L. et al. [1987] *Science* 237:779–781; McGrane, V. et al. [1988] *Am J. Trop. Med. Hyg.* 39:502–510; Morris, A. C. et al. [1989] *Med. Vet. Entomol.* 3:1–7). Transformation was achieved occasionally, but at very low frequencies and apparently was independent of P element-mediation. The rare transformation events reported appear to be the result of random integrations. Present evidence indicates the utility of P element vectors is limited in organisms outside the family Drosophilidae (O'Brochta, D. A., A. M. Handler [1988] *Proc. Natl. Acad. Sci. USA* 85:6052–6056).

Given the current absence of efficient vectors for arthropods other than Drosophila, substantial research has been devoted to developing alternative DNA delivery systems. Investigators have explored ballistic introduction of DNA-coated microprojectiles (Baldarelli, R. M., J. A. Lengyel [1990] *Nucl. Acids. Res.* 18:5903–5904; Carlson, D. A. et al. [1989] In: *Host Regulated Developmental Mechanisms in Vector Arthropods*, Borovsky, D. and Spielman, A., eds., Univ. of Florida Press, Vero Beach. Fla., pp. 248–252), electroporation, and puncturing eggs with DNA-coated silicon carbide filaments. Another potential DNA delivery system involves binding heterologous DNA to sperm and introducing it through artificial insemination. This approach may be useful in honey bees (Milne, C. P. et al. [1988] *J. of Agri. Research* 27(2):84–89, but it is not known whether the bound DNA can actually be introduced into the embryo by this method.

Aspects of the subject invention have been reported in Presnail, J. K. and M. A. Hoy (1992) *Proc. Natl. Acad. Sci. USA* 89:7732–7736.

BRIEF SUMMARY OF THE INVENTION

A method for transforming an arthropod is provided by the present invention. The method involves microinjecting a nucleic acid sequence encoding a desired trait into the reproductive tract of a female arthropod before oviposition. Transgenic arthropods that contain a recombinant nucleic acid sequence introduced into the arthropod or an ancestor of the arthropod are also included in the invention. The transformation method is useful for arthropods that have not previously been amenable to transformation, and also provides a simpler method than those that have been previously used for arthropods. Methods for controlling the population of an arthropod are also included, as are methods of increasing the effectiveness of arthropods as biological control agents. Further, the transformation methods may be used to improve the mass rearing capability of arthropods.

BRIEF DESCRIPTION OF THE DRAWINGS

FIG. 1(A–B). Map of the plasmid pJKP2 and associated PCR primers. (A) pJKP2 was produced by introducing a 500 bp BamHI/EcoRI fragment containing the hsp70 promoter into the polylinker of pDM79. (B) The location of the PCR primers in relation to the hsp70/lacZ region of plasmid pJKP2.

BRIEF DESCRIPTION OF THE SEQUENCES

SEQ ID NO. 1 is PCR primer JKP2-1 according to the subject invention.

SEQ ID NO. 2 is PCR primer JKP2-2 according to the subject invention.

SEQ ID NO. 3 is PCR primer JKP2-21 according to the subject invention.

DETAILED DISCLOSURE OF THE INVENTION

The present invention relates to a method for DNA-mediated transformation of arthropods. Advantageously, the transformation method is useful for a wide variety of arthropods, including some for which no transformation method is currently available.

Arthropods are divided into two subphyla, Chelicerata and Mandibulata. Mandibulata includes the insects and those related to them. Chelicerata includes the class Arachnida, among others. Included among the arthropods that may be transformed by the method of the subject invention are economically important mandibulate arthropods such as the mosquito and other insects. Furthermore, the subject invention may also be utilized with cheliterate arthropods such as members of the class Arachnida. The class Arachnida includes ticks and other members of the order Acarina. In addition to ticks, the order Acarina includes mites such as those of the family Phytoseiidae.

The methods of the subject invention can be used to produce a wide range of transgenic arthropods including both chelicerates and mandibulates. This is the first time that transgenic arthropods of the subphylum Chelicerata have been produced.

The method of the subject invention is particularly useful for the Phytoseiidae species *Metaseiulus occidentalis* (Nesbitt), which is an important biological control agent. Additional economically important Phytoseiidae species for which maternal microinjection is particularly useful include, for example, *Amblyseius victoriensis*, *Amblyseius barkeri*, *Phytoseiulus persimilis*, *Typhlodromus pyri*, *Amblyseius potentillae*, *Amblyseius andersoni*, *Amblyseius fallacis*, *Amblyseius gossipi*, *Phytoseilus macropilis*, *Amblyseius californicus*, *Amblyseius hibisci*, *Euseius* (=Typhlodromus) *finlandicus*, *Amblyseius longispinosus*, and *Typhlodromus caudiglans*.

Understanding of the present invention is facilitated by the following definitions:

"Oviposition" refers to the act of laying or depositing eggs by the female member of an arthropod species.

The "reproductive tract" of a female arthropod comprises reproductive organs of the female, including a single ovary or a pair of ovaries that are connected to a lateral oviduct. The lateral oviducts join to form a median oviduct that opens posteriorly into a genital chamber. Sometimes the genital chamber will form a tube, the vagina, and a bursa copulatrix for reception of the penis. Opening from the genital chamber or the vagina is a spermatheca. Accessory glands may also be present. Preferably the ovaries and most preferably the ovarioles are targeted by the microinjection methods described herein.

"Increased pesticide resistance" refers to an arthropod being more tolerant of a certain level of a pesticide than a native or "wild-type" arthropod of the same species. A dose of pesticide that kills or inhibits the growth of a native arthropod but does not have the same effect on an arthropod having increased pesticide resistance is termed a "discriminating dose."

Similarly, "decreased pesticide resistance" refers to an arthropod being less tolerant of a certain level of a pesticide than a native or "wild-type" arthropod of the same species.

A "recombinant" nucleic acid sequence refers to a nucleic acid sequence that has been isolated from its natural surroundings, i.e. the chromosome, and linked to other nucleic acid sequences to which it is not naturally found linked.

As used herein, "exogenous DNA" refers to DNA which does not naturally occur in a particular organism.

A "transgenic" arthropod carries a gene or genes that have been introduced into the germine of the arthropod, or an ancestor of the arthropod, at an early (usually one-cell) development stage. The term "carries" refers to the genes being maintained in the cells of the arthropod, either as autonomous nucleic acids or by integration into the arthropod genome.

"Sterility" refers to the loss of an arthropod's ability to reproduce. Causes of sterility include defects in egg or sperm development, blockages that prevent fertilization, and other defects in the reproductive system of a male or female arthropod.

A "biological control agent" is a living organism, such as an arthropod, that is useful for the control of pests. Parasitic and predaceous arthropods are particularly useful as biological control agents.

The transformation method of the preferred embodiment of the subject invention is termed "maternal microinjection" and involves microinjecting a solution containing a nucleic acid sequence into an arthropod reproductive tract before oviposition. Maternal microinjection has several advantages over previous arthropod transformation systems. Not only does maternal microinjection allow DNA-mediated transformation of arthropods for which transformation was not previously possible, but maternal microinjection is also much less laborious than methods that involve microinjection of preblastoderm eggs, which is the method described for use in Drosophila. Maternal microinjection also causes lower mortality and higher transformation frequencies than observed in, for example, mosquito microinjection (Miller, L. et al. supra; McGrane, V. et al., supra; Morris, A. C. et al., supra; Walker, V. K. [1990] In: *Advances in Cell Culture*, Vol. 7, Ed. Maramorosch, K., Academic Press, NY, pp. 87–124).

Dechorionation of the eggs to be transformed is not required for maternal microinjection, in contrast to other arthropod microinjection methods. These previously reported methods require dechorionation to allow the egg to be penetrated by the needle and to allow desiccation so that solutions of exogenous DNA can be injected. An intact chorion is important in maintaining adequate water balance in the developing embryos, so mortality is increased by dechorionation. Dechorionation is a significant factor in the mortality rate associated with microinjection of insect eggs also, because excessive desiccation can be lethal. A further advantage of maternal microinjection is that the microinjected eggs are incubated inside the female until oviposition, which may increase the survival rate.

We have demonstrated that maternal microinjection is an effective means for transforming arthropods. Steps previously thought to be necessary for transformation of arthropods surprisingly need not be performed. Further, transformation by the methods described here results in the stable establishment of a desired trait in future generations of the microinjected arthropods.

Maternal microinjection may be performed using a needle that is commonly used for microinjection. To penetrate the female arthropod, less flexible needles than those used for Drosophila eggs are preferred (see, e.g., Santamaria, P. [1986] In: *Drosophila: A Practical Approach*, Ed. Roberts, D. B., IRL Press, Oxford, pp. 159–173). Such needles may be pulled from microcapillary tubes (1.0 mm external diameter, 0.5 mm internal diameter) with an internal glass filament. An automatic needle puller may be used to produce needles having a fine (1 μm) short tip. Prior to microinjection, the tip of the needle is commonly broken off to produce a jagged tip approximately three μm in diameter. A needle having a jagged tip combined with the internal filament is preferred for phytoseiid mites. The needles most suitable for other arthropods may be easily determined by testing various available needles.

Prior to performing maternal microinjection, the arthropods to be injected are immobilized in a manner appropriate for the subject arthropod. One suitable immobilization method is to place two layers of double stick tape lengthwise on a microscope slide. The tape is then cut at approximately a 45° angle to produce a ledge under which the arthropods may be secured. Other methods of immobilizing the arthropods to be microinjected may be used, such as anesthetization. Care must be taken to select females with eggs that are nearly, but not fully, mature. Fully mature eggs may burst when probed with the injection needle, leading to death of the egg and female.

Nucleic acid sequences are microinjected into the reproductive tract of female arthropods, preferably into the ovary, and most preferably into the ovariole. The microinjected nucleic acid sequences are taken up most readily if injected before the chorion is fully developed. Phytoseiid females are usually microinjected between the third and fourth coxae. In species of arthropods such as mites, in which the ovary region of the organism is semi-translucent, the reproductive tract is visible through the microscope and injection is visually facilitated.

In species that are more opaque, such as *Cardiochiles diaphaniae*, an initial dissection can be performed to identify the region of the ovary and a corresponding exterior point for injection. For microinjection of large arthropods, a small piece of exoskeleton may be removed to allow visual identification of the ovary and allow direct injection into it. The piece of exoskeleton is then replaced and sealed with paraffin to reduce water loss and mortality. Microinjection is performed with the aid of an inverted compound microscope.

After injection, the female arthropods are carefully lifted from the tape to a clean region of the slide. When fully dry, the arthropods are removed from the slide and placed individually on a support such as leaf discs (isolated on water-saturated cotton) or other appropriate support. An appropriate food is also provided. The females are typically observed daily, dead females are removed, and those depositing eggs are maintained on fresh supports. The eggs produced by the injected females are considered the $G_0$ generation. $G_1$ progeny are assayed for transformation using an appropriate assay.

For example, arthropods that have been transformed with a pesticide resistance gene may be selected by treating appropriate life stages with discriminating concentrations of the pesticide and allowing the survivors to mate and reproduce. Techniques that may be used include topical application of pesticide, residue tests, slide dip tests, feeding tests, and other selection or screening techniques known to those skilled in the art.

The nucleic acid sequences that are maternally microinjected according to the present invention will commonly include a nucleotide sequence that codes for and imparts upon the transformed arthropod a desired trait. Such traits include, for example, increased resistance to pesticides for a beneficial arthropod, increased pesticide susceptibility for harmful arthropods, sterility of the offspring of transformed pest arthropods, detectable markers that are useful for monitoring an arthropod population, altered sex ratio, altered temperature or humidity tolerance, altered ability to diapause or not, altered prey or host range, altered ability to disperse, reduced ability to vector human, plant, or animal diseases, improved response by natural enemies to cues produced by pest arthropods, and other traits that one skilled in the art would consider useful. It should be noted that, for purposes of monitoring arthropod populations, it is not necessary for the exogenous DNA to be expressed. Rather, the mere presence of the DNA (detectable by PCR, for example) is sufficient to monitor the population.

The nucleic acid sequences to be maternally microinjected is commonly "operably linked," or placed into a functional relationship, with another nucleic acid sequence. For instance, a promoter or enhancer is operably linked to a coding sequence if it affects the transcription of the sequence. Generally, operably linked means that the nueleic acid sequences being linked are contiguous and, where necessary to join two protein coding regions, contiguous and in reading frame.

Techniques for nucleic acid manipulation, such as subcloning nucleic acid sequences encoding polypeptides into expression vectors, labelling probes, DNA hybridization, and so on are described generally, for example, in Sambrook et al. (1989) *Molecular Cloning: A Laboratory Manual* (2nd ed.), Vols. 1–3, Cold Spring Harbor Laboratory, NY.

The nucleic acid sequences that are maternally microinjected into arthropods according to the present invention are often incorporated into "expression vectors," "cloning vectors," or "vectors," which are often plasmids or other nucleic acid molecules that are able to replicate in a chosen host cell. Vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in an arthropod cell for expression. Most typically, the vectors used in the present invention replicate in the arthropod by integrating into the arthropod genomic DNA.

Expression vectors contain, in addition to those elements described above, sequences for controlling expression of a gene operably linked to these control sequences. Such an expression "cassette" may contain a promoter, an enhancer and necessary processing information sites, such as ribosome-binding sites, RNA splice sites, polyadenylation sites, transcriptional terminator sequences and mRNA stabilizing sequences. Control sequences will be chosen so that the sequences are functional in the desired host cell or organism. The expression vectors used in the present invention can contain control sequences that function in the arthropod to be transformed. These control sequences are typically from other arthropods and may be heterologous (for example, Drosophila control sequences function in the mite *M. occidentalis*), or may be homologous (a gene from the arthropod to be transformed may be cloned, its control sequences identified, and these sequences then linked to the gene encoding the desired trait by methods known to those skilled in the art).

A useful, but not necessary element of an expression or other vector is one or more selectable or screenable markers. A selectable marker may be a gene that codes for a protein necessary for the survival or growth of a host cell or organism under selected conditions. The presence of this gene ensures the growth of only those host cells or organisms that contain the vector. Typical selection genes encode proteins that (a) confer resistance to antibiotics or other toxic substances, e.g., pesticides, ampicillin, neomycin, methotrexate, etc.; (b) complement auxotrophic deficiencies, or (c) supply critical nutrients not available from complex media. The choice of the proper selectable marker will depend on the host cell, and appropriate markers for different hosts are well known in the art. Often, the vectors useful in the present invention will contain two selectable markers, one for use in *E. coli* during the construction and amplification of the vector, and the other for use in the arthropod to be transformed.

Included among the nucleic acid sequences that encode desirable traits and also function as selectable markers are the parathion hydrolase (opd) gene from *Pseudomonas diminuta* (Serdar, C. M., D. T. Gibson [1985] *Bio/Technology* 3:567–571; Serdar, C. M. et al. [1989] *Bio/Technology* 7:1151–55) and the neomycin resistance (neo) gene (Steller, H., V. Pirrotta [1985] *EMBO J.* 4: 167–171), which confers resistance to the antibiotic G418. In one embodiment of the invention, the opd gene is functionally linked to an actin 5C promoter (Bond, B. J., N. Davidson [1986] *Mol. Cell. Biol.* 6:2080–2088). Ice nucleation genes (e.g. iceE from *E. herbicola*, Orser, C. S. et al. [1983] *Molecular Genetics of the Bacterial-Plant Interaction*, Ed. Puhler, A. pp. 353–361; inaZ from *P. syringae*, Green, R. L. et al. [1985] *Nature* 317:645–648; and others) may be used to confer traits upon arthropods as another means to improve the control of their population.

Selectable markers transformed into arthropods by the method of the present invention are useful, for example, to produce transgenic arthropods for genetic control programs. A selectable marker may be used for sexing arthropods by targeting the marker to the male-specific Y chromosome. The transformed arthropods are maintained under selection so that only males grow. The males are then sterilized and released into the wild to serve as a biological control agent. Such sterile release programs are discussed in, for example, Knipling, E. F. (1955) *J. Econ. Entomol.* 48:4559–4562.

The method is also useful for monitoring dispersal of an arthropod. The arthropods are transformed by microinjecting a nucleic acid sequence into the reproductive tract of a female arthropod before oviposition, the nucleic acid sequence encoding a detectable marker. A transformed arthropod that carries the detectable marker is selected and introduced into an arthropod population to be monitored. By monitoring the frequency at which the detectable marker is found in the population over time, one can determine how rapidly or how far the marker has spread. As noted above, the DNA itself may act as the detectable marker and, therefore, need not be expressed.

In the present invention, the selectable marker may be the gene encoding the desired trait, for example, if the desired trait is pesticide resistance. Alternatively, the selectable marker may be used to select those arthropods that have been transformed by the vector, while the desired trait is encoded by a nucleic acid sequence other than the selectable marker. For example, the desired trait may be a screenable or detectable marker, which is a gene that codes for a protein whose activity is easily detected, allowing arthropods expressing such a marker to be readily identified. Such markers include, for example, β-galactosidase, β-glucuronidase, and luciferase. The selectable marker and the detectable marker may be contained on the same or different cloning vectors.

After microinjecting the nucleic acid sequence encoding these markers, the arthropods are fed the substrate, which prevents growth of those arthropods not containing a functional selectable marker. Those arthropods capable of growth on the substrate are then tested for stability of the transforming nucleic acid sequences by passing the substrate-resistant arthropods through several generations and determining whether the substrate resistance is maintained.

MATERIALS AND METHODS

Figure 1A:
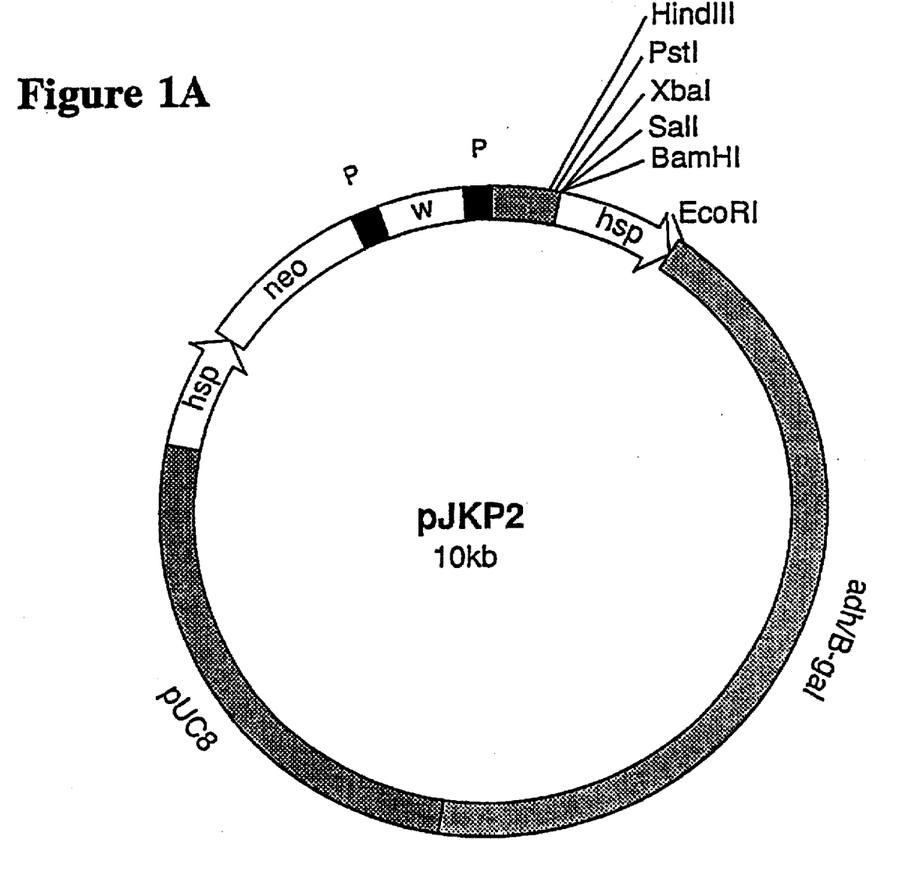

Construction of cloning vector. A 500 base pair (bp) BamHI/EcoRI fragment containing the *D. melanogaster* hsp70 heat-shock promoter (Lis, J. T. et al. [1983] *Cell* 35:403–410) was isolated from the plasmid pHSS7/hsp (Siefert, H. S. et al. [1986] *Proc. Natl. Acad. Sci. USA* 83:735–739) by restriction endonuclease digestion and gel purification. This fragment was ligated into the BamHI/EcoRI polylinker sites of the P element vector pDM79 (Mismer, D., G. M. Rubin [1987] *Genetics* 116:565–578). The resulting plasmid (pJKP2) carries the Drosophila hsp70 promoter 5' to the adh/lacZ fusion gene of pDM79 (FIG. 1A). The plasmid was transformed into *E. coli* strain DH5α. Approximately 100 μg of plasmid were isolated from 50 ml of bacterial culture using a QIAGEN-tip 100® column (Qiagen, Inc., Chatsworth, Calif.). The plasmid preparation was resuspended in injection buffer (5 mM KCl, 0.1 mM PO$_4$, pH 7.8) (Spradling, A. C. [1986] In: *Drosophila: A Practical Approach*, supra, pp. 175–196) at a concentration of 300 µg/ml.

The construct pJKP2 was first tested for lacZ expression in transiently-transformed *D. melanogaster* larvae and expression was determined to be regulated in a heat-shock dependent manner. No β-galactosidase activity was detected in uninjected *M. occidentalis* for up to four hours after immersion, but endogenous β-galactosidase activity could be detected in uninjected *M. occidentalis* larvae if larvae were incubated in the X-gal solution for over five hours.

Colony source and culture methods. The strain of *M. occidentalis* used in these studies (known as Pullman blackberries) was originally collected in 1987 near Pullman, Wash. on blackberry bushes. It is highly susceptible to all pesticides tested. The colony is maintained in 10×10 cm trays on wax-coated paper resting on top of water-saturated cotton. An open water barrier, approximately 1 cm wide, surrounds the cotton. The trays are placed in a plastic box with a 1 cm petroleum jelly barrier at the top of the box. The *M. occidentalis* mites were fed a mixture of two-spotted spider mite, *Tetranychus urticae*, and Pacific spider mite, *Tetranychus pacificus*. The spider mites, which were originally collected in the field, were grown on bean plants.

Microinjection of gravid *M. occidentalis* females. Preliminary studies indicated that the needles used to inject *D. melanogaster* eggs were too flexible to penetrate *M. occidentalis* females. We therefore pulled needles from microcapillary robes (1.0 mm external diameter, 0.5 mm internal diameter) with an internal glass filament. An automatic needle puller produced needles with a fine (1 µm) short tip. Prior to microinjection, the tip of the needle was broken off to produce a jagged tip approximately three µm in diameter. Microinjection was performed with the aid of a ZEISS inverted compound microscope at approximately 200X magnification.

Figure 2:
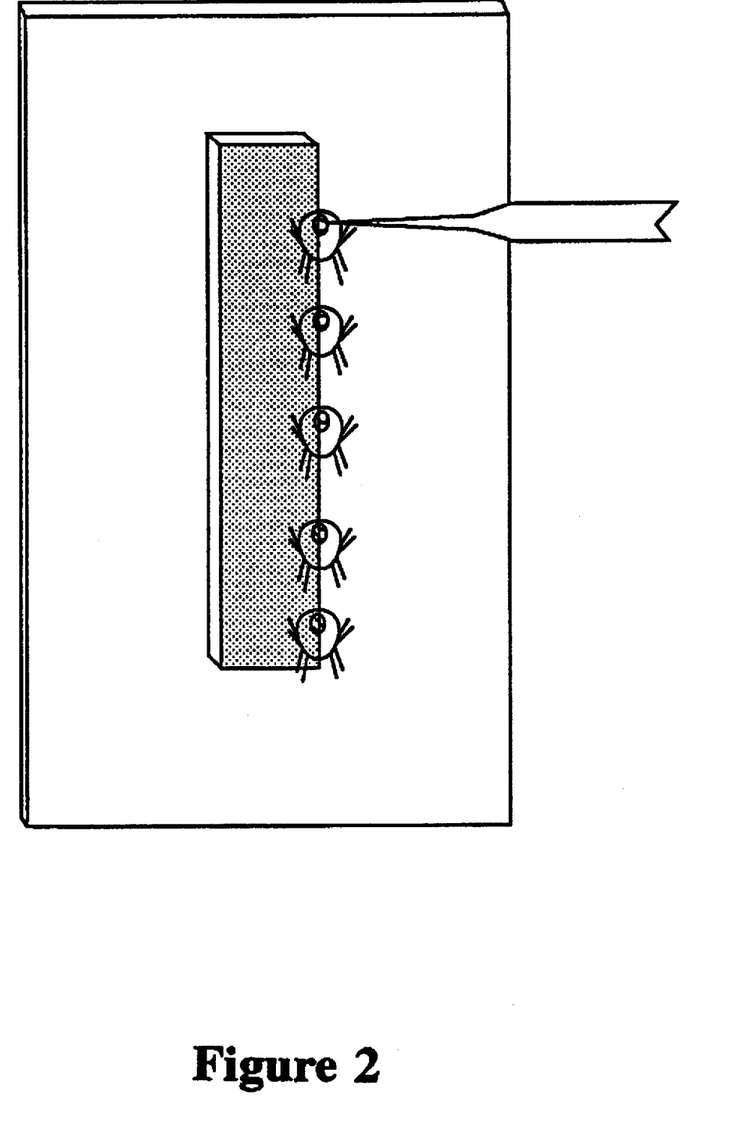
FIG. 2. Gravid females of *M. occidentalis* to be microinjected are positioned under two layers of double-stick tape that has been cut to produce an overhanging ledge. Microinjection is in the posterior region and may be made directly into the egg.

Mites were prepared for injection in the following manner. Two layers of SCOTCH® brand double stick tape. (3M, Minneapolis, Minn.) were placed lengthwise on a microscope slide. The tape was then cut at approximately a 45° angle to produce a ledge under which the mites could be secured. Adult gravid females were secured under the overhanging ledge of the tape in a lengthwise orientation (FIG. 2). Only females with eggs that are nearly, but not fully, mature were selected. Ten females were aligned and covered with distilled water. Females were injected between the third and fourth coxae in dose proximity to the egg.

After injection, the mites were carefully lifted from the tape to a clean region of the slide. When fully dry, the mites were removed from the slide and placed individually on pinto bean leaf discs (isolated on water-saturated cotton) with spider mite prey. Females were observed daily, dead females were removed, and those depositing eggs were maintained on fresh leaf discs. The eggs produced by the injected females are considered the G$_0$ generation. G$_1$ progeny were assayed for transformation using a β-galactosidase assay.

Heat-shock and β-galactosidase assay. G1 larvae were covered with water and exposed to a standard heat-shock of 37° C. for 30 minutes. After heat-shock, the water was removed and the mites were submersed in 50 mM NaPO$_4$ (pH 8.6). An X-gal solution [0.3% X-gal (in dimethyl formamide), 30% FICOLL (Pharmacia LKB Biotechnology, Piscataway, N.J.), 50 mM NaPO$_4$ (pH 8.6), 2 mM K$_4$Fe(CN)$_6$, 2 mM K$_4$Fe(CN)$_6$] was added and the mites' abdomens were punctured. The larvae were kept at 100% relative humidity and after three hours were scored for presence or absence of blue color.

DNA extraction. DNA was extracted from individual adult mites by the CHELEX® method. Specimens were frozen in liquid N$_2$ and ground to powder, 100 µl of a 5% Chelex (BioRad, Richmond, Calif.) solution were added, and the samples were mixed thoroughly with a vortex mixer. The samples were then heated to 56° C. for 15 minutes followed by 4 minutes at 100° C. The samples were then centrifuged in a microfuge for two minutes, and the DNA supernatant removed for PCR analysis.

Figure 1B:
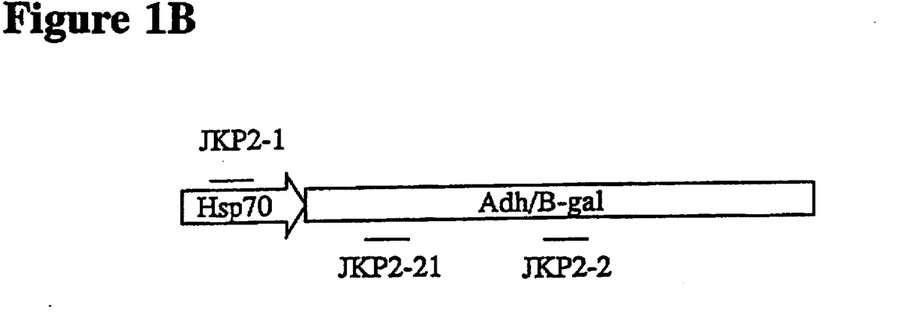

Oligonucleotide primers for PCR. A 30 bp synthetic oligomer (JKP2-1; SEQ ID NO. 1) identical to region 126–155 of the Drosophila hsp70 heat-shock promoter was used in conjunction with two primers from the *E. coli* lacZ region of the plasmid pJKP2. JKP2-2 (SEQ ID NO. 2; complementary to the 426–475 region of lacZ), in conjunction with JKP2-1, amplifies a 930 bp fragment. JKP2-21 (SEQ ID NO. 3; complimentary to the 267–294 region of lacZ), in conjunction with JKP2-1, amplifies a fragment internal to the above mentioned product. The plasmid pJKP2 and associated oligonucleotide primers are illustrated in FIG. 1B and C.

Ten microliter aliquots of DNA extracted from individual G$_6$ adult females derived from lines expressing β-galactosidase in the G$_1$ generation were amplified for 32 cycles under standard reaction conditions (Saiki, R. K. [1990] In: *PCR Protocols, A Guide to Methods and Applications*, Eds. Innis, M. A. et al., Academic Press, San Diego, pp. 13–21) using a thermal cycler from Coy Laboratory Products (Ann Arbor, Mich.). The first cycle consisted of four minutes at 95° C., 30 seconds at 63° C., and 90 seconds at 75° C. The remaining 31 cycles consisted of 30 seconds at 95° C., two minutes at 63° C., and 90 seconds at 75° C.

PCR products were electrophoresed at 30 mA for three hours on a 1% agarose Tris-borate-EDTA (TBE) gel as described in Sambrook et al., supra. The gel was then stained with ethidium bromide and photographed.

Following are examples which illustrate procedures, including the best mode, for practicing the invention. These examples should not be construed as limiting. All percentages are by weight and all solvent mixture proportions are by volume unless otherwise noted.

EXAMPLE 1

Maternal Microinjection of *M. occidentalis*

Microinjection of gravid females. Table 1 provides the results of microinjecting gravid *M. occidentalis* females. The average survival of females after 24 hours was 49%, although the number of survivors continued to decline over the next 24 hours to approximately 30%. Seventy-eight (19%) of the treated females produced between one and eight eggs. From these 78 females, 48 lines were established (established lines are defined as those producing G$_1$ larvae).

β-Galactosidase assay. To determine whether the exogenous DNA was maintained in the progeny of the microinjected mites, β-galactosidase was assayed. Of the 48 established lines, seven expressed β-galactosidase in the G$_1$ larvae. Two of these putatively-transformed lines were lost, perhaps due to poor rearing conditions or decreased fitness. The five remaining lines were maintained and analyzed by PCR.

PCR analysis. To determine whether the transforming plasmid was stably integrated into the transformed mites, the mites were passed through six generations, after which DNA was extracted. The DNA was subjected to PCR analysis using probes specific for the plasmid pJKP2 to determine whether plasmid sequences were present in the progeny. In control PCR reactions, at annealing temperatures below 63° C., amplification of pJKP2 resulted in nonspecific products. At an annealing temperature of 66.5° C., only the two predicted bands are produced in sufficient quantity to be visible by ethidium bromide/UV analysis. At temperatures above 53° C., no amplification products were observed from DNA extracted from uninjected M. occidentalis.

PCR was first performed in the presence of the hsp70 primer (JKP2-1; SEQ ID NO. 1) and the external lacZ primer (JKP2-2; SEQ ID NO. 2). The reaction produced the 930 bp product predicted from the plasmid sequence. The identity of this amplification product was confirmed by removing an aliquot of this reaction and conducting a second PCR reaction using the hsp70 primer and the internal lacZ primer (JKP2-21; SEQ ID NO. 3). Again, the product was of the predicted size consistent with amplification of sequences derived from the introduced plasmid. Both products span the border between the Drosophila hsp70 and the *E. coli* lacZ genes. It is unlikely that products of the specific sizes predicted could be produced from endogenous DNA sequences. Further, no amplification was observed from samples of uninjected M. occidentalis. The inheritance of plasmid sequences in the $G_6$ generation demonstrates that stable transformation has been achieved.

| No. injected | % survival | No. laying eggs | No. established lines | No. expr. $G_1$ lacZ | No. $G_6$ tested with PCR |
|---|---|---|---|---|---|
| 50 | 50 | 12 | 4 | 0 | — |
| 50 | 24 | 5 | 3 | 1 | —* |
| 50 | 36 | 12 | 9 | 0 | — |
| 50 | 66 | 11 | 10 | 1 | —* |
| 20 | 70 | 6 | 2 | 0 | — |
| 60 | 48 | 13 | 13 | 4 | 2 |
| 75 | 57 | 16 | 7 | 1 | 0 |
| 50 | 42 | 3 | 0 | 0 | — |
| 405 | 49 | 78 | 48 | 7 | 2 |

*the colony was lost before the PCR assay.

Because the efficiency of maternal microinjection is high compared to other methods, this procedure provides a DNA delivery system for species for which no vector system is available. The frequency of transformation may be increased by using a vector such as the P-element vectors used in Drosophila.

EXAMPLE 2

Persistence of Microinjected DNA in *Metaseiulus occidentalis*

Females injected with three different concentrations of DNA were assayed by hemi-nested PCR analysis during a 24 hour period to determine whether the plasmid DNA persisted over this period. The effect of three different concentrations of plasmid DNA on transmission to the first five eggs deposited after microinjection was also investigated.

Colony source and maintenance. In this study, we used the carbaryl, organophosphorus, and sulfur-resistant strain (COS) of M. occidentalis, which was maintained and reared as previously-described (Hoy, M. A., K. A. Standow [1982] *Entomol. Exp. & Appl.* 31:316–323; Roush, R. T., M. A. Hoy [1981] *J. Econ. Entomol.* 74:138–141; Hoy, M. A. [1982] "Genetics and genetic improvement of the Phytoseiidae," In *Recent Advances in Knowledge of the Phytoseiidae*, M. A. Hoy, ed., University of California Publ. No. 3284, Berkeley). After injection, individual M. occidentalis were transferred to leaf discs (approximately 1 cm diameter) with prey (a mixture of *Tetranychus urticae* and *T. pacificus*).

Microinjection of M. occidentalis. To determine how long DNA persisted in microinjected females, 35 females were injected with plasmid (250 μg/ml) and held for varying periods before placing them at –80° C. Four females each were harvested at 0, 1, 2, 3, 4, 12, and 24 hours. DNA was extracted and analyzed by hemi-nested PCR as described below.

To assess the frequency at which DNA is found in the eggs laid after microinjection with different concentrations of DNA, one- and two-day old M. occidentalis females were injected with three concentrations of plasmid DNA. Fifty mites were injected with each concentration. The fifty females were then divided into five groups of ten. The first group was allowed to lay one egg before the egg and female were collected separately onto 0.5 ml Eppendorf microcentrifuge tubes and stored at –80° C. The second group of ten females was allowed to lay to eggs before collecting the second egg and the female. In a similar fashion, females and eggs were collected in the third, fourth, and fifth groups. In all cases, the eggs and females were stored at –80° C. until the DNA was extracted for PCR analysis.

DNA extraction. Macerated samples were suspended in a 5% solution of Chelex® 100 resin (Bio-Rad Laboratories, Richmond, Calif.) and held at 56° C. for 15 minutes, followed by incubation at 100° C. for four minutes. Samples were then centrifuged briefly and placed at –20° C. until PCR analysis.

PCR methods. To determine the presence of the plasmid pJKP2 in the samples, we employed sequential hemi-nested PCR. Samples were first amplified by PCR for 30 cycles using external primers (jkp2-1, jkp2-2; SEQ ID NOS. 1 and 2, respectively), which span the Drosophila hsp70/*E. coli* β-galactosidase border producing a 930 bp product (Presnail, J. K, M. A. Hoy [1992] *Proc. Natl. Acad. Sci USA* 89:7732–7736). A 1.0 μl aliquot of the first reaction was then subjected to a second round of PCR with one of the original primers (jkp2-1; SEQ ID NO. 1) and a second internal primer (jkp2-21; SEQ ID NO. 3), which generated an approximately 700 bp product. PCR reactions were run with the standard concentrations of reagents: 50 mM KCl, 10 mM Tris-HCl, 1.5 mM $MgCl_2$, 0.2 μM each primer, 200 μM each dNTP, and 0.8 unit Taq polymerase.

The following precautions were exercised to avoid contamination in the hemi-nested PCR reactions. Aeroseal® pipette tips (USA Scientific, Ocala, Fla.) were employed for all pipetting of PCR reactants. Additionally, the first PCR reactions were overlayed with 400 μl of mineral oil. When transferring an aliquot of the first reaction to the second reaction, 99 μl of the mineral oil was withdrawn into the pipette tip before withdrawing one μl of the PCR product. In this way, a mineral oil barrier was maintained between the sample and the micropipette and between the PCR reactions and the benchtop. To be certain no contamination was occurring between samples, the positive control (100 pg pJKP2 as the template) was the first reaction in every series of samples. A negative control was the second reaction. Hence, any carryover from the positive control should have been found in the negative control. To further examine potential carryover problems, we ran a preliminary series of alternating positive (reactions spiked with 100 pg pJKP2) and negative (no template added) reactions to assess the potential carryover of template or PCR products. No products were observed in the (-) lanes. For each group of reactions, a master mix containing all the PCR reactants except the template DNA was prepared. The master mix was added to all reactions and a final aliquot was analyzed by PCR for potential contamination. This final aliquot acted as a further negative control to assess potential carryover between samples. Samples were placed in a Coy Tempcycler II, model 110 (Coy Corp., Grass Lake, Mich.) and subjected to 30 of the following temperature cycles for both PCR amplifications: 92° C. for 30 seconds, 65° C. for 30 seconds, and 75° C. for one minute. Following PCR, the samples were analyzed by gel electrophoresis.

Electrophoresis. Samples were electrophoresed through a 1.5% agarose TBE gel for two hours at 60 mA. The gels were then stained in ethidium bromide, placed on a transilluminator, and photographed.

Results. PCR analysis revealed persistence of DNA in 82% of the 28 females tested over the 24-hour period examined (Table 2). Plasmid DNA was found in all of the females immediately after injection (0 hour). The PCR product in these samples was visible after the first reaction. In the one-hour samples, three of four produced a visible PCR product in the first reaction, and all four had visible products after the second hemi-nested reaction. In the two-hour samples, only one sample produced a visible product after the first reaction, but three of the four produced PCR products in the second reaction. The three-, four-, and twelve-hour samples produced results similar to the two-hour samples. In the 24-hour samples, three of four *M. occidentalis* females produced PCR products that were visible after the first reaction. These results indicate that plasmid DNA persisted in the majority of injected females for at least 24 hours, indicating the plasmid sequences persist long enough to be passed to more than one egg. Most phytoseiid females deposit 1–3 eggs per day.

TABLE 2

Analysis by hemi-nested PCR of *M. occidentalis* females to determine the presence of plasmid DNA during the 24 hours following maternal microinjection

| Time (hours) | No. positive in 1st reaction[a] | Additional no. positive in 2nd reaction[b] | Total no. positive females |
|---|---|---|---|
| 0 | 4 | 0 | 4 |
| 1 | 3 | 1 | 4 |
| 2 | 1 | 2 | 3 |
| 3 | 1 | 2 | 3 |
| 4 | 1 | 2 | 3 |
| 12 | 1 | 2 | 3 |
| 24 | 3 | 0 | 3 |
| Total (% +) | 15 (53%) | 8 (29%) | 23 (82%) |

[a]PCR reactions were examined for presence of a 930 bp fragment.
[b]The second round of hemi-nested PCR produced a 700 bp fragment.

The results from injecting three concentrations of DNA (250, 500, and 750 ng/µl) indicate that the plasmid DNA (injected into the gravid *M. occidentalis* females) was passed to 71% of the 72 eggs deposited (Table 3). After the females had deposited either 1, 2, 3, 4, or 5 eggs, the female and her last egg were analyzed by hemi-nested PCR. PCR-positive eggs were found in the first through the fifth eggs collected. If the results of all three plasmid concentrations are combined, 87% (n=23) of the first eggs were positive by hemi-nested PCR, 60% (n=15) of second eggs, 64% (n=14) of third eggs, 61% (n=13) of fourth, and 71% (n=7) of fifth eggs deposited. Although the first egg was apparently more likely to contain plasmid sequences (87%±13), the results indicate that more than 63% (±9) of succeeding eggs contained the plasmid as well.

TABLE 3

Analysis of maternally microinjected *M. occidentalis* females and eggs

| Group | 250 ng/µl | | 500 ng/µl | | 750 ng/µl | |
|---|---|---|---|---|---|---|
| | females | eggs | females | eggs | females | eggs |
| 1st egg | 1/7 | 5/7 | 7/10 | 9/10 | 6/6 | 6/6 |
| 2nd egg | 3/5 | 4/5 | 3/5 | 2/5 | 3/5 | 3/5 |
| 3rd egg | 2/3 | 3/3 | 3/4 | 3/4 | 4/7 | 3/7 |
| 4th egg | 5/6 | 4/5 | 3/4 | 2/4 | 3/4 | 2/4 |
| 5th egg | 0/0 | 0/0 | 4/4 | 3/4 | 3/3 | 2/3 |
| Positive total | 13/21 | 16/20 | 20/27 | 19/27 | 12/25 | 16/25 |
| % positive | 65 | 80 | 74 | 70 | 76 | 64 |

The percentage of *M. occidentalis* females that died before laying any eggs was similar for all three DNA concentrations (38% at 750 ng/µl, 26% at 500 ng/µl, 36% at 250 ng/µl). The percentage of females in this study that died prior to laying the number of eggs required of them was 42% at 750 ng/µl, 48% at 500 ng/µl, and 56% at 250 ng/µl.

EXAMPLE 3

Microinjection of *Amblyseius finlandicus*

In *A. finlandicus*, persistence of plasmid DNA (250 µg/ml) was analyzed by hemi-nested PCR in every fifth egg deposited by maternally microinjected females until their death. *A. finlandicus* was maintained on pinto bean leaves and fed a mixture of apple and cherry pollen. After injection, individual *A. finlandicus* females were transferred to individual leaves and provided with pollen.

Microinjection of *A. finlandicus*. Thirty three-day old gravid *A. finlandicus* were injected and every fifth egg deposited was collected until the females died. The eggs were placed in 0.5 ml microcentrifuge tubes and held at –80° C. prior to DNA extraction.

PCR products were observed in all *A. finlandicus* egg cohorts except the last. The percentage of positive eggs decreased from 79% of the first eggs produced to 56% of the fifth, 70% of the tenth, 18% of the 15th, 44% of the 20th, and 14% of the 25th eggs produced. The decreasing percentage of PCR-positive eggs, along with the decreasing numbers of eggs per cohort, indicate it may be most efficient to collect eggs from microinjected females only up to the tenth egg. The tenth eggs are deposited, on average, eight days after microinjection.

Of the 24 females microinjected, five died within the first 24 hours and produced no eggs, but the remaining 19 produced at least one egg, and 16 produced five eggs or more. The average number of eggs produced by the 24 females was 13.4 (S.E.=12.4) over an average oviposition period of 10.5 days (S.E.=8.0) for a mean oviposition rate of 1.3 eggs/female/day.

DNA concentration does not appear to affect the transmission rate. However, high DNA concentrations resulted in needle clogging. The DNA used in these studies was purified using a QIAGEN® Tip 100 column (QIAGEN Inc., Chatsworth, Calif.). With different DNA purification techniques, difficulties with needle clogging could possibly be avoided, but these data do not suggest higher levels of positive would occur with higher plasmid concentrations.

Hemi-nested PCR provides an accurate and sensitive method for DNA detection. Based on data from preliminary experiments in which a serial dilution of plasmid DNA was spiked into a PCR reaction in the presence of *M. occidentalis* DNA, we could obtain detectable PCR products in the second reaction from as few as four copies of plasmid. Over 100 copies of plasmid DNA were required to produce a consistently viable product in the single PCR reactions. Theoretically, stable transformation requires only a single plasmid.

Identification of all potential transformants therefore required the increased sensitivity of hemi-nested PCR. Because hemi-nested PCR requires homology over a greater length of sequence than PCR with only two primers, the fidelity of the reactions was also improved.

EXAMPLE 4

Transformation of *Cardiochiles diaphaniae*

We conducted experiments which show the utility of the subject invention in transforming the endoparasitie wasp *Cardiochiles diaphaniae*. The first experiment was to determine whether microinjected water containing food coloring would be taken up by ovaries. Preliminary dissections indicated this species has two ovaries, each ovary being bilobed and uniting in a bulb-like structure and connected by lateral oviducts to a common oviduct leading to the ovipositor.

Figure 3:
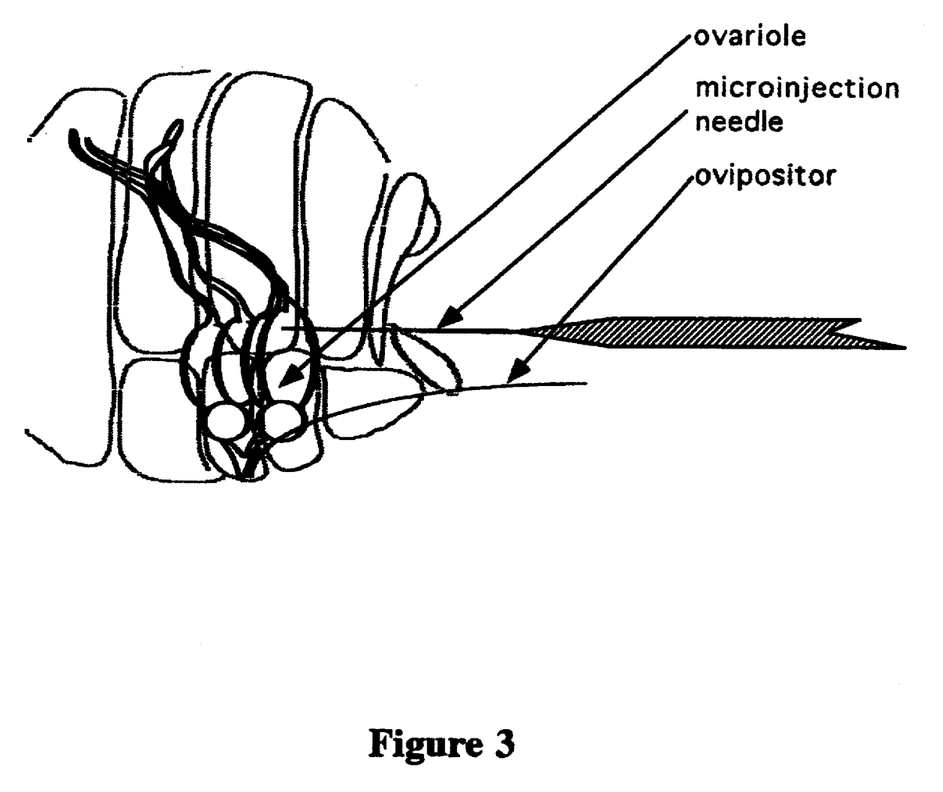
FIG. 3. Maternal microinjection of *Cardiochiles diaphaniae*. The diagram represents the general location of the right ovaries and of the inserted needle.

Ten females were injected in the area around the ovipositor. The needle, drawn to the same dimensions as the needle used for *Metaseiulus occidentalis* and *Amblyseius finlandicus*, was inserted as denoted in FIG. 3. The ovaries of the injected females were dissected shortly after microinjection. Of the ten injected females, four displayed colored ovaries. Coloration was limited to only one of the ovaries. This is probably a result of injecting the wasps on only one side of the ovipositor.

The eggs from the colored ovaries were removed from the ovary and examined. Several (ca. 20) of the eggs from each colored ovary displayed the altered coloration. Several water-injected females were allowed to recover and placed in an arena with their lepidopteran host the melonworm *Diaphania hyalinata*. The injected wasps, after recovering from etherization, behaved normally and vigorously oviposited on their hosts.

The next experiment was to determine whether an injected solution having exogenous DNA (also containing food coloring) would also be taken up by the ovaries and the eggs within. Sixteen females were injected, four of which displayed altered coloration of their ovaries. In one case, where both sides of the female were injected, both ovaries displayed altered coloration.

The ovaries were washed with three aliquots of TE buffer to remove any DNA from the exterior of the ovaries. DNA was then extracted from the individual samples, both colored and uncolored, and the samples were PCR amplified for the presence of the injected exogenous plasmid DNA. The exogenous DNA was detected by PCR.

EXAMPLE 5

Maternal Microinjection of the Parasitic Wasp *Trioxys pallidus* (Hymenoptera: Aphidiidae)

Maternal microinjection of *Trioxys pallidus* may be achieved by anesthetizing adult females with carbon dioxide and immobilizing them on a glass slide using double-stick tape. The needle used to microinject these wasps is modified by adjusting its diameter, length, and tip shape (jagged or smooth) to optimize the efficacy of microinjection. Because *Trioxys pallidus* is darkly pigmented and heavily sclerotized, dissection is conducted to determine the locations of the ovaries. Preferably, the needle is inserted into the female through a less-heavily sclerotized intersegmental membrane.

After microinjection, the adult females are placed into cages with their host aphids (*Chromaphis juglandicola* Kaltenbach) on Persian walnut tree plants (*Juglans regia* L.) to oviposit. Parasite wasps oviposit into the host aphids. The parasitized aphids are reared and the adult wasps that emerge are screened after having been allowed to reproduce. For example, if the opd gene is microinjected, the transformants are screened using a plastic cup bioassay technique (Hoy, M. A., F. E. Cave [1991] *Biocontrol Sci. and Technology* 1:31–41). The cup used in this bioassay contains residues of azinphosmethyl or another organophosphorous insecticide such as parathion.

Alternatively, the progeny are screened by polymerase chain reaction analysis.

EXAMPLE 6

Monitoring Dispersal of *Aphytis melinus* DeBach

The parasitic wasp *A. melinus* DeBach (Insecta, Hymenoptera Aphelinidae) is an effective biological control agent of California red scale, *Aonidiella aurantii* (Maskell), in citrus. Large-scale releases of *A. melinus* are made by growers after purchasing the parasites from commercial insectaries. At present, little is known about the dispersal propensity or distances travelled of these augmentatively-released natural enemies of California red scale.

*A. melinus* can be transformed by microinjection as described in Example 1, except that host scale insects (*Aspidiotus nerii* Bouche) on pink banana squash, *Cucurbita maxima* Duchesne, can be provided to the microinjected females. The progeny of individual females are reared in individual cages and then screened by PCR.

Preferably, the DNA marker that is inserted will be unique and specific. To facilitate choosing such a DNA marker sequence, PCR reactions are carried out on *A. melinus* that has been obtained from commercial insectaries and from field-collected colonies in the region of interest. Primers derived from candidate marker sequences are tested. The unique marker sequences may be inserted into several lines and the number of insertions and their effect on fitness evaluated. A population cage technique (Rosenheim, J. A., M. A. Hoy [1988] *J. Econ. Entomol.* 81:476–483) may be used to examine the effect of the marker sequences on life history attributes such as fecundity, sex ratio, development rate, and longevity.

The DNA marker may be a unique random sequence, or the DNA may code for a protein, such as a selectable or screenable marker. For example, the β-galactosidase gene linked to appropriate control sequences may be used as the marker. In this case, the presence of the marker gene may be confirmed by β-galactosidase assay instead of, or in addition to, the PCR assay.

Once an appropriate line containing the desired marker has been identified, the line is mass-reared and released into citrus groves. Collections of parasitized California red scale are made at different sites around the release site and estimates are made of the direction, rate, and distances travelled by the released parasites. Because indigenous, untransformed A. *melinus* are typically present, the transformed DNA marker allows a determination of whether a specific A. *melinus* individual was among those released, or the progeny of a released transformed individual. The $F_1$ progeny of transformed individuals are likely to carry the marker, so information may be obtained regarding how long the parasites persist in the orchard.

EXAMPLE 7

Controlling the Populations of Pest Species

For many genetic control programs, males are required and females are unwanted. Maternal microinjection can be used to facilitate separating out a specific sex. A nucleic acid sequence that codes for susceptibility or resistance to a chemical is inserted into sex-determining chromosomes. Selection is then applied to eliminate the unwanted sex. Alternatively, antisense nucleic acids may be injected that alter normal sex determination to produce the desired sex.

An alternative means of controlling the population of a pest species is to use maternal microinjection to insert genes that confer lowered fitness. Both sexes are mass-reared and released. The transformed arthropods mate with wild arthropods and the trait is transmitted to the $F_1$ and subsequent generations. Environmental stresses then induce mortality. Traits that are useful include increased susceptibility to freezing, increased susceptibility to high temperatures, and altered sex ratios.

It is to be understood that the above description is intended to be illustrative and not restrictive. Many embodiments will be apparent to those of skill in the art upon reviewing the above description. The scope of the invention should, therefore, be determined not only with reference to the above description, but should also be determined with reference to the appended claims, along with the full scope of equivalents to which such claims are entitled.

What is claimed is:

1. A method for producing an arthropod transformed with a heterologous DNA sequence, wherein said method comprises:

injecting said DNA sequence into the reproductive tract of a gravid female arthropod, wherein said injection is prior to oviposition such that transformed ova result, and wherein said arthropod is member of an arthropod family selected from the group consisting of Aphidiidae, Aphelinidae and Phytoseiidae; and permitting said transformed ova to develop into a transformed arthropod.

2. The method of claim 1, wherein said arthropod is a member of the family Phytoseiidae.

3. The method of claim 2, wherein said arthropod is a member of the species *Metaseiulus occidentalis*.

4. The method of claim 1, wherein said arthropod is a member of the family Aphidiidae.

5. The method of claim 1, wherein said arthropod is a member of the family Aphelinidae.

6. The method of claim 1, wherein said DNA sequence encodes a detectable marker.

7. The method of claim 6, wherein said detectable marker is β-galactosidase.

* * * * *

UNITED STATES PATENT AND TRADEMARK OFFICE
CERTIFICATE OF CORRECTION

PATENT NO. : 5,702,932

DATED : December 30, 1997

INVENTOR(S) : Marjorie A. Hoy and James K. Presnail

It is certified that error appears in the above-identified patent and that said Letters Patent is hereby corrected as shown below:

Column 3, line 58: "cheliterate" should read --chelicerate--.

Column 4, line 19: "oviduet" should read --oviduct--; and line 47: "germine" should read --germline--.

Column 9, line 32: "robes" should read --tubes--; and line 50: "dose" should read --close--.

Column 15, line 23: "endoparasitie" should read --endoparasitic--.

Signed and Sealed this

Seventh Day of April, 1998

Attest:

BRUCE LEHMAN

Attesting Officer      Commissioner of Patents and Trademarks